United States Patent [19]

Sato et al.

[11] 4,379,148

[45] Apr. 5, 1983

[54] ANALGESIC AND ANTI-INFLAMMATORY COMPOSITION

[75] Inventors: Makoto Sato, Moriyama; Isami Kimura; Azuma Yamaguchi, both of Shiga, all of Japan

[73] Assignee: Morishita Pharmaceutical Co., Ltd., Osaka, Japan

[21] Appl. No.: 342,963

[22] Filed: Jan. 26, 1982

[30] Foreign Application Priority Data

Jan. 30, 1981 [JP] Japan .................................. 56/13523

[51] Int. Cl.³ .................... A61K 27/00; A61K 31/625
[52] U.S. Cl. ................................ 424/232; 424/248.57
[58] Field of Search ................ 424/248.4, 248.56, 232, 424/248.57

[56] References Cited
PUBLICATIONS

Takaya et al., J. Med. Chem., 22, p. 53, (1979).
Merck Index, 9th Ed., (1976), 874, 4796, 4845, 5154 and 7078.

Primary Examiner—Stanley J. Friedman
Attorney, Agent, or Firm—Sughrue, Mion, Zinn, Macpeak & Seas

[57] ABSTRACT

An analgesic and anti-inflammatory composition containing emorfazone (4-ethoxy-2-methyl-5-morpholino-3(2H)-pyridazinone) and a non-steroidal acidic anti-inflammatory agent such as phenylbutazone, ibuprofen, mefenamic acid, indomethacin, acetylsalicylic acid, naproxen, ketoprofen and flurbiprofen.

4 Claims, No Drawings

ANALGESIC AND ANTI-INFLAMMATORY COMPOSITION

FIELD OF THE INVENTION

The present invention relates to a pharmaceutical composition and, more particularly, to an analgesic and anti-inflammatory composition for oral administration comprising emorfazone (4-ethoxy-2-methyl-5-morpholino-3(2H)-pyridazinone) and a non-steroidal acidic anti-inflammatory agent, as main components.

BACKGROUND OF THE INVENTION

Hitherto, non-steroidal acidic anti-inflammatory agents such as acetylsalicylic acid, phenylbutazone, ibuprophen, indomethacin and the like have been widely used in the fields of surgery and internal medicine as analgesic and anti-inflammatory agents, with fairly satisfactory results. The pharmacological activity which is common to the non-steroidal acidic anti-inflammatory agents is inhibitory activity on the biosynthesis of prostaglandin; and this mechanism of action is considered to be that which induces the desired analgesic and anti-inflammatory activities, as reported by R. J. Flower et al., *Biochemical Pharmacol.*, 23, 1439 (1974). In other words, the non-steroidal acidic anti-inflammatory agents only inhibit the biosynthesis of prostaglandin which is a factor for strengthening pain and inflammation in the living body; and, therefore, the analgesic and anti-inflammatory activities of these non-steroidal acidic anti-inflammatory agents are generally mild. [See, S. H. Ferreira, *Nature*, 240, 200 (1972)] Further, these agents have been reported as having serious side-effects such as gastrointestinal disorders and edema formation based on the inhibitory activity of prostaglandin biosynthesis. [See, P. W. Dodge et al., *Anti-Inflammatory Drugs*, edited by J. R. Vane and S. H. Ferreira, Springer-Verlag, p. 280, Berlin (1979)]

To solve such disadvantages of non-steroidal acidic anti-inflammatory agents, an extensive study has been made mainly from the standpoint of pharmaceutical preparations such as prodrugs, suppositories or preparations for external use in order to minimize or eliminate side-effects. That is, the most important problem regarding the existing non-steroidal acidic anti-inflammatory agents is how to utilize these agents most effectively.

In a series of studies on emorfazone, 4-ethoxy-2-methyl-5-morpholino-3(2H)-pyridazinone, the present inventors have found that emorfazone is a non-steroidal basic anti-inflammatory agent which does not inhibit the biosynthesis of prostaglandin; thus, emorfazone differs from the existing non-steroidal acidic anti-inflammatory agents. As a result of further studies, the present inventors have found that a combination of emorfazone and a non-steroidal acidic anti-inflammatory agent described above exhibits an excellent synergistic effect for analgesic activity and an additive or synergistic effect for anti-inflammatory activity, while the composition causes markedly decreased gastric disorders as a main side-effect inherent to the non-steroidal anti-inflammatory agents. Accordingly, the present invention is based on a finding that the dosage level of non-steroidal inflammatory agents can be decreased and simultaneously the toxicity and the side-effects inherent to these agents can be reduced by administering the non-steroidal acidic anti-inflammatory agents in combination with emorfazone.

SUMMARY OF THE INVENTION

An object of the present invention is to provide an excellent analgesic and anti-inflammatory composition comprising emorfazone and a non-steroidal acidic anti-inflammatory agent as main components.

Another object of the present invention is to provide a pharmaceutical composition for oral use comprising emorfazone and a non-steroidal acidic anti-inflammatory agent.

A further object of the present invention is to provide a pharmaceutical composition comprising a non-steroidal acidic anti-inflammatory agent in synergistic combination with emorfazone.

Still another object of the present invention is to provide a pharmaceutical composition containing emorfazone and a non-steroidal acidic anti-inflammatory agent, said composition being characterized by enhanced pharmacological activity coupled with reduced side effects as compared to the use of the non-steroidal acidic anti-inflammatory agent above.

Other objects of this invention will be apparent from the Detailed Description of the Invention, hereinbelow.

DETAILED DESCRIPTION OF THE INVENTION

One of the anti-inflammatory agents, emorfazone, used in the present invention is chemically 4-ethoxy-2-methyl-5-morpholino-3(2H)-pyridazinone and is disclosed in Japanese Patent Publication No. 32754/70 and M. Takaya et al., *J. Med. Chem.*, 22, 53 (1979).

The non-steroidal acidic anti-inflammatory agents which can be used in the present invention are phenylbutazone, ibuprofen, mefenamic acid, indomethacin, acetylsalicylic acid, naproxen, ketoprofen, flurbiprofen and the like.

The present invention provides a combination of emorfazone and a non-steroidal acidic anti-inflammatory agent. Therefore, any non-steroidal agent having an analgesic and anti-inflammatory effect due to its inhibitory activity on the biosynthesis of prostaglandin can be used singly or as a mixture thereof in the present invention in combination with emorfazone.

The proportional amounts of emorfazone and of the non-steroidal acidic anti-inflammatory agent in the composition of this invention will vary depending upon the selection of non-steroidal anti-inflammatory agent used.

However, one advantage of the present invention is that both ingredients of the composition of this invention can be used in dosages significantly reduced from their respective dosages when employed individually. As a general guideline, the composition of this invention, comprises (A) emorfazone in an amount of about ¼ to about ½ of the clinically effective amount (ED$_{50}$) of emorfazone when used alone and (B) a non-steroidal acidic anti-inflammatory agent in an amount of about ⅓ to about ½ of the clinically effective amount (ED$_{50}$) of the non-steroidal acidic anti-inflammatory agent used alone.

For example, emorfazone is generally used alone at a daily dose of about 600 mg for subjects having a body weight of 60 kg (e.g., about 10 mg/kg) by oral administration and, therefore, can be used orally at a daily dose of from about 2.5 mg/kg (i.e., ¼ dose of 10 mg) to about 5 mg/kg (i.e., ½ dose of 10 mg) in combination with a non-steroidal acidic anti-inflammatory agent according to the present invention.

On the other hand, clinically effective amounts of acidic anti-inflammatory agents for oral administration vary widely depending upon the particular agent selected; typical agents and daily doses thereof are shown in Table 1 below.

TABLE 1

| Non-Steroidal Anti-inflammatory Agent | Daily Dose (oral) (Body Weight: 60 kg) (mg) |
|---|---|
| Phenylbutazone | 200–600 |
| Ibuprofen | 600–1600 |
| Mefenamic Acid | 600–1600 |
| Indomethacin | 50–200 |
| Acetylsalicylic Acid | 1500–5000 |
| Naproxen | 200–800 |
| Ketoprofen | 100–300 |
| Flurbiprofen | 100–300 |

For example, phenylbutazone is generally used at a daily dose of about 200 mg to about 600 mg for subjects having a body weight of 60 kg (i.e., about 3.3 mg/kg to about 10 mg/kg) for oral administration and, therefore, can be used orally at a daily dose of from about 1.1 mg/kg (i.e., ⅓ dose of 3.3 mg) to about 5 mg/kg (i.e., ½ dose of 10 mg) in combination with about 2.5 mg/kg to 5 mg/kg of emorfazone.

It is to be noted, however, that the dosage levels of the non-steroidal anti-inflammatory agents described above are typical examples and can vary depending upon the severity of conditions to be treated, the sensitivity of the subject to the specific agent and the like; therefore, the present invention is not limited to the above dosages nor to the specific proportions of emorfazone and non-steroidal acidic anti-inflammatory agent disclosed hereinbefore.

Dry oral pharmaceutical compositions comprising the two active ingredients of this invention in combination can be manufactured utilizing conventional powder-forming, capsule-making, tablet-making and the like techniques. For example, the pharmaceutical composition comprising emorfazone and a non-steroidal acidic anti-inflammatory agent for oral administration according to the present invention can be prepared by mixing the active ingredients with other additives such as excipients and lubricating agents, for example, lactose, starch, hydroxypropyl cellulose, crystalline cellulose, magnesium stearate, anhydrous silicic acid and the like which are well known in the art for use in preparing pharmaceutical preparations for oral administration, to prepare a powder preparation, and, if desired, filling hard capsules with the resulting powder. Also, a granule preparation can be prepared from the above powder using a pelletor, and a tablet preparation can be prepared by compressing the granules by means of a tabletting machine. In any event, the manipulative techniques for preparing dry oral compositions are well-known in the art.

It may be convenient that such tablets or capsules contain, in each dosage form, about 100 mg of emorfazone and an appropriate amount of a non-steroidal acidic anti-inflammatory agent or a mixture of two or more non-steroidal acidic anti-inflammatory agents.

The present invention is further illustrated by the following Examples and Reference Examples, but is not intended to be limited by the specific ingredients, formulations, dosages and the like of these Examples.

REFERENCE EXAMPLE 1

Analgesic Test by Phenylquinone Writhing Method

Male ddY mice (18–22 g) fasted for 18 hours were divided into test groups and a control group of 7 animals per group. According to the method of Siegmund et al. (*Proc. Soc. exp. Biol. Med.*, 95, 729, 1957), 10 ml/kg of 0.02% p-phenylquinone was injected into the peritoneal cavity of all of the mice 30 minutes after the oral administration of the test drugs to the test groups. The number of writhes was counted for 20 minutes after the p-phenylquinone injection. The $ED_{50}$ was the dose that reduced the number of writhes of the control group by 50%, and was calculated by the method of Litchfield and Wilcoxon (*J. Pharmacol. exp. Ther.*, 96, 99, 1949). The $ED_{50}$ value for emorfazone was 40 mg/kg. The results obtained are shown in Table 2 below.

TABLE 2

| Drugs | Emorfazone 0 | 10 | | 20 | |
|---|---|---|---|---|---|
| Phenybutazone | 66 | 32 | (49.5) | 16 | (33) |
| Ibuprofen | 13.5 | 8 | (10.1) | 3 | (6.8) |
| Mefenamic acid | 36 | 21 | (27) | 13 | (18) |
| Indomethacin | 0.52 | 0.33 | (0.39) | 0.18 | (0.26) |
| Acetylsalicylic acid | 155 | 115 | (116.3) | 40 | (77.5) |
| Naproxen | 9 | 6.2 | (6.3) | 4.1 | (4.5) |
| Ketoprofen | 0.5 | 0.37 | (0.38) | 0.23 | (0.25) |
| Flurbiprofen | 2 | 6.2 | (8) | 0.8 | (1) |

$ED_{50}$ value of emorfazone was 40 mg/kg (p.o.). All numerical values are indicated in terms of mg/kg (p.o.). Numbers in parenthesis are the theoretical additive doses. The other numbers are the doses obtained experimentally.

The effect of the combination of emorfazone with phenylbutazone is hereinafter described in detail. As is apparent from the results in Table 2, the $ED_{50}$ value of phenylbutazone was 66 mg/kg while the $ED_{50}$ for emorfazone was 40 mg/kg as noted above. If ½ of the $ED_{50}$ of emorfazone (20 mg/kg) were given to animals together with ½ of the $ED_{50}$ of phenylbutazone (33 mg/kg), an additive $ED_{50}$ value should be theoretically obtained. However, the dose of phenylbutazone obtained experimentally was 16 mg/kg. If ¼ of the $ED_{50}$ of emorfazone (10 mg/kg) were used, the dose of phenylbutazone which would be theoretically required to obtain an additive $ED_{50}$ value, is 49.5 mg/kg (¾ of the $ED_{50}$), but the dose obtained experimentally was only 32 mg/kg. These results indicate that the analgesic activity of phenylbutazone is potentiated by the emorfazone. Thus, the above experiment shows that the combined effect of emorfazone with such non-steroidal anti-inflammatory drugs as phenylbutazone, ibuprofen, mefenamic acid, indomethacin, acetylsalicylic acid, naproxen, ketoprofen and flurbiprofen was for the most part a synergistic response. It should be noted that even where the synergy is low, perhaps yielding only an additive effect, that the present invention is still highly useful in permitting one to lessen the side effects of the non-steroidal acidic anti-inflammatory agent.

REFERENCE EXAMPLE 2

Analgesic Test by Randall-Selitto Method

Male Wistar rats (120–140 g) fasted for 18 hours were divided into test groups and a control group of 5 animals per group. According to the method of Randall and Selitto (*Arch. int. Pharmacodyn.*, 111, 409, 1957) and Winter et al. (*Proc. Soc. exp. Biol. Med.*, 111, 544, 1962), 0.1 ml of a 1% carrageenin suspension dissolved in physiological saline was injected subcutaneously into the plantar surface of the hind paw of each control animal and also of each test animal immediately after the oral administration of the test drugs. The pain threshold was measured after the carrageenin injection at hourly intervals for 3 hours with an analgesy meter (Ugo Basile, Milan). The $ED_{50}$ was defined as the dose that increased the mean value of the pain threshold of the control group by 50%, and was determined from the dose-response curves. The results are shown in Table 3. Concerning the inflammatory pain provoked by carrageenin, the analgesic activities of the non-steroidal anti-inflammatory drugs were found to be markedly potentiated by their use in combination with emorfazone.

TABLE 3

| Drugs | Emorfazone 0 | 4.5 | | 9 | |
|---|---|---|---|---|---|
| Phenylbutazone | 125 | 22 | (93.8) | 19 | (62.5) |
| Ibuprofen | 120 | 10 | (90) | 8 | (60) |
| Mefenamic acid | 120 | 58 | (90) | 20 | (60) |
| Indomethacin | 6.8 | 0.8 | (5.1) | 0.3 | (3.4) |
| Acetylsalicylic acid | 340 | 240 | (255) | 70 | (170) |
| Naproxen | 240 | 160 | (180) | 60 | (120) |
| Ketoprofen | 6 | 3 | (4.5) | 1 | (3) |
| Flurbiprofen | 22 | 15 | (16.5) | 2 | (11) |

$ED_{50}$ value of emorfazone was 18 mg/kg (p.o.). All numerical values are indicated in terms of mg/kg (p.o.). Numerical values in parenthesis are theoretical additive doses. The other numerical values are the doses obtained experimentally.

REFERENCE EXAMPLE 3

Anti-inflammatory Test by Whittle's Method

Male ddY mice (18–22 g) fasted for 18 hours were divided into test groups and a control group of 7 or 8 animals each. According to the method of Whittle (*Brit. J. Pharmacol.*, 22, 246, 1964), 10 ml/kg of 4% pontamine sky blue dissolved in physiological saline was injected intravenously to all animals 30 minutes after the oral administration of the test drugs. Ten minutes later, 10 ml/kg of 0.7% acetic acid dissolved in physiological saline was injected intraperitoneally into all animals and 20 minutes thereafter the animals were sacrificed. The amount of the dye in the peritoneal exudate was determined at 590 nm by using a spectrophotometer (Hitachi Instrument Co.). The $ED_{30}$ was defined as the dose which decreased the amount of dye of the control group by 30%, and was determined graphically.

The results obtained are shown in Table 4. Essentially all doses calculated theoretically on an additive basis were about equal to those obtained experimentally, indicating that according to this test procedure the anti-inflammatory activity of the combination of emorfazone with a non-steroidal anti-inflammatory drug is an additive effect. Of course, as noted above, even an additive effect is advantageous in reducing the side-effects, particularly of the gastric disorder type, of the non-steroidal acidic anti-inflammatory agents.

TABLE 4

| Drugs | Emorfazone 0 | 28.8 | | 86 | |
|---|---|---|---|---|---|
| Phenylbutazone | 175 | 130 | (131.3) | 86 | (87.5) |
| Ibuprofen | 76 | 56 | (57) | 37 | (38) |

TABLE 4-continued

| Drugs | Emorfazone 0 | 28.8 | | 86 | |
|---|---|---|---|---|---|
| Mefenamic acid | 82 | 60 | (61.5) | 41 | (41) |
| Indomethacin | 2.2 | 1.6 | (1.65) | 1 | (1.1) |
| Acetylsalicylic acid | 225 | 160 | (168.8) | 110 | (112.5) |
| Naproxen | 12 | 8.5 | (9) | 5.8 | (6) |
| Ketoprofen | 3.2 | 2.2 | (2.4) | 1.3 | (1.6) |
| Flurbiproben | 4 | 2.8 | (3.0) | 1.9 | (2) |

$ED_{30}$ value of emorfazone was 115 mg/kg (p.o.). All numerical values are indicated in terms of mg/kg (p.o.). Numerical values in parenthesis are theoretical additive doses. The other numerical values are the doses obtained experimentally.

REFERENCE EXAMPLE 4

Anti-inflammatory Test in Adjuvant-induced Arthritis

Female Sprague-Dawley rats (180–220 g) were used. A modification of the method of Ward et al. (*Clin. Res.*, 14, 172, 1966) was used for this experiment. On day 0 of the test, the adjuvant containing 0.6 mg of Mycobacterium butylicum (Difco) in 0.1 ml of liquid paraffin was injected into the plantar surface of the right hind paw. The test drugs were administered orally once a day for 15 days. The severity of inflammation of the 4 paws and the tail of each rat was evaluated visually at day 30 and scored by a point system. The grading for each lesion was on a 0 to 3 scale with 0 indicating absence of inflammation and 3 indicating maximum inflammation. Arthritic score was defined as the total scores which were observed in the 4 paws and the tail of each animal. The results obtained are shown in Table 5 below.

The inhibitory effects of ibuprofen, mefenamic acid, ketoprofen, indomethacin, naproxen and flurbiprofen were significantly potentiated by the combination with 100 mg/kg of emorfazone, which did not show any significant effect when used alone. The inhibitory effects of acetylsalicylic acid and phenylbutazone were not essentially affected by the combination thereof with the same dose of emorfazone.

TABLE 5

| Drugs | Dose (mg/kg, p.o.) | Arthritic score Test drugs alone-treated | Combination (with 100 mg/kg Emorfazone) |
|---|---|---|---|
| Control | | 10.9 ± 1.0 | |
| Emorfazone | 100 | 10.9 ± 1.0 | |
| Phenylbutazone | 15 | 3.3 ± 0.3 (70) | 3.7 ± 0.4 (66) |
| Ibuprofen | 25 | 7.5 ± 1.0 (31) | 3.6 ± 0.6* (67) |
| Mefenamic acid | 25 | 6.7 ± 0.8 (39) | 4.2 ± 0.5* (61) |
| Indomethacin | 0.1 | 8.9 ± 0.9 (18) | 7.6 ± 1.1* (30) |
| Acetylsalicylic acid | 100 | 7.6 ± 1.2 (30) | 7.9 ± 0.6 (27) |
| Naproxen | 1 | 5.3 ± 0.7 (51) | 2.1 ± 0.6* (81) |
| Ketoprofen | 2 | 7.8 ± 1.1 (28) | 3.6 ± 0.9* (67) |
| Flurbiprofen | 2 | 6.5 ± 0.9 (40) | 3.4 ± 0.6* (69) |

Each numerical value represents the mean (arthritic score) ±S.E. of 7–10 rats.
Numerical values in parenthesis are the inhibitory percentages.
*$p < 0.05$: Significant difference from corresponding group treated with non-steroidal anti-inflammatory drug alone.

REFERENCE EXAMPLE 5

Acute Toxicity Test

Male ddY mice (18–22 g) fasted for 18 hours were divided into groups of 10 animals each. The $LD_{50}$ was calculated from the lethality within 7 days after the oral administration of test drugs according to the method of Litchfield and Wilcoxon (*J. Pharmacol. Exp. Ther.*, 96, 99, 1949). The results obtained are shown in Table 6 below.

In contrast to the analgesic and anti-inflammatory action, the $LD_{50}$ values obtained experimentally were much greater than those calculated theoretically, indicating that the effect of combining emorfazone with non-steroidal anti-inflammatory drugs was an antagonistic one. Therefore, safety margin is increased by the use of the present invention.

TABLE 6

| Drugs | Emorfazone | | | |
|---|---|---|---|---|
| | 0 | 240 | | 480 |
| Phenylbutazone | 570 | 480 | (427.5) | 380 (285) |
| Ibuprofen | 1150 | 1300 | (862.5) | 1400 (575) |
| Mefenamic acid | 1190 | 920 | (892.5) | 610 (595) |
| Indomethacin | 11.3 | 13 | (8.5) | 18 (5.7) |
| Acetylsalicylic acid | 1260 | 1000 | (945) | 650 (630) |
| Naproxen | 1180 | 1200 | (885) | 1200 (590) |
| Ketoprofen | 305 | 380 | (228.8) | 400 (152.5) |
| Flurbiprofen | 210 | 155 | (157.5) | 130 (105) |

$LD_{50}$ value of emorfazone was 960 mg/kg (p.o.). All numerical values are indicated in terms of mg/kg (p.o.). Numerical values in parenthesis are theoretical additive doses. The other numerical values are the doses obtained experimentally.

REFERENCE EXAMPLE 6

Effect on Gastric Irritation

The effects of emorfazone on the gastric damage induced by non-steroidal anti-inflammatory drugs were studied in male Wistar rats (140–160 g). Groups of rats, fasted for 24 hours, were given orally the doses of emorfazone and of the non-steroidal anti-inflammatory drugs as set forth in Table 7. Four hours later, the animals were sacrified with ether, and the stomach, opened along the great curvature, was examined macroscopically. Pontamine sky blue (1%, 5 ml/kg) was injected intravenously 30 minutes before ether inhalation in order to be able to visually observe ulcers and hemorrhage (Brodie et al: *Science*, 170, 183, 1970). The results obtained are shown in Table 7 below. The concomitant administration of 50 or 100 mg/kg of emorfazone never enhanced but tended to inhibit ulcers induced by the non-steroidal anti-inflammatory drugs.

TABLE 7

| Drugs | | Emorfazone | | |
|---|---|---|---|---|
| | | 0 | 50 | 100 (mg/kg) |
| Phenylbutazone | (200) | 29.4 ± 2.7 | 26.6 ± 6.7 | 22.6 ± 1.7 |
| Ibuprofen | (200) | 28.2 ± 3.8 | 15.7 ± 6.1 | 17.5 ± 2.6 |
| Mefenamic acid | (300) | 10.5 ± 2.7 | 7.3 ± 1.9 | 10.2 ± 2.6 |
| Indomethacin | (20) | 7.1 ± 3.1 | 5.9 ± 2.6 | 6.0 ± 0.8 |
| Acetylsalicylic acid | (300) | 10.0 ± 1.7 | 2.8 ± 1.5 | 10.0 ± 1.5 |
| Naproxen | (100) | 8.0 ± 1.6 | 5.1 ± 2.1 | 8.0 ± 1.2 |
| Ketoprofen | (100) | 9.5 ± 2.4 | 4.2 ± 2.0 | 7.8 ± 1.7 |
| Flurbiprofen | (50) | 9.8 ± 2.6 | 7.2 ± 2.8 | 10.0 ± 3.6 |

Each numerical value represents the mean value (ulcer index: mm)±S.E. of 5–10 animals. Numerical values in parenthesis are the doses used of the non-steroidal anti-inflammatory drugs. Ulcers were never observed with emorfazone alone.

EXAMPLE 1

| Emorfazone | 100 g |
|---|---|
| Ibuprofen | 50 g |
| Lactose | 65 g |
| Starch | 27 g |
| Hydroxypropyl Cellulose | 6 g |
| Magnesium Stearate | 2 g |
| Total | 250 g |

Emorfazone, ibuprofen, lactose and starch were mixed uniformly, and hydroxylpropyl cellulose dissolved in an appropriate amount of a solvent was added to the mixture. The resulting mixture was then granulated and, after drying, the granules were regulated, mixed with magnesium stearate and compressed by a tabletting machine to prepare 1000 tablets, each weighing 250 mg.

EXAMPLE 2

In the same manner as described in Example 1, 1000 tablets, each weighing 250 mg, were prepared from the following formulation.

| Emorfazone | 100 g |
|---|---|
| Phenylbutazone | 50 g |
| Lactose | 65 g |
| Starch | 27 g |
| Hydroxypropyl Cellulose | 6 g |
| Magnesium Stearate | 2 g |
| Total | 250 g |

EXAMPLE 3

In the same manner as described in Example 1, 1000 tablets, each weighing 200 mg, were prepared from the following formulation.

| Emorfazone | 100 g |
|---|---|
| Indomethacin | 15 g |
| Lactose | 52 g |
| Starch | 25 g |
| Hydroxypropyl Cellulose | 6 g |
| Magnesium Stearate | 2 g |
| Total | 200 g |

EXAMPLE 4

| Emorfazone | 100 g |
|---|---|
| Ibuprofen | 50 g |
| Lactose | 400 g |
| Starch | 150 g |
| Crystalline Cellulose | 100 g |
| Hydroxypropyl Cellulose | 50 g |
| Total | 850 g |

Emorfazone, ibuprofen, lactose, starch and crystalline cellulose were mixed uniformly and granulated using a pelletor. After regulating the resulting granules, the granules were dried to obtain a granule preparation.

EXAMPLE 5

| Emorfazone | 100 g |
|---|---|
| Phenylbutazone | 50 g |
| Crystalline Cellulose | 30 g |
| Lactose | 60 g |

| -continued | |
|---|---|
| Anhydrous Silicic Acid | 10 g |

Crystalline cellulose, lactose and anhydrous silicic acid were added to emorfazone and phenylbutazone and, after mixing uniformly, hard capsules were filled with the mixture. Each capsule contained 250 mg of the mixture.

While the invention has been described in detail and with reference to specific embodiments thereof, it will be apparent to one skilled in the art that various changes and modifications can be made therein without departing from the spirit and scope thereof.

What is claimed is:

1. An analgesic and anti-inflammatory pharmaceutical composition for oral administration comprising an analgesic and anti-inflammatory effective amount of a combination of 4-ethoxy-2-methyl-5-morpholino-3(2H)-pyridazinone and a non-steroidal acid anti-inflammatory agent selected from the group consisting of phenylbutazone, ibuprofen, mefenamic acid, indomethacin, acetylsalicylic acid, naproxen, ketoprofen and flurbiprofen, said composition comprising about ¼ to ½ of the oral clinically effective amount of 4-ethoxy-2-methyl-5-morpholino-3(2H)-pyridazinone and about ⅓ to ½ the oral clinically effective amount of the non-steroidal acid anti-inflammatory agent.

2. The pharmaceutical composition of claim 1, including a pharamceutically acceptable carrier.

3. A process for potentiating the pharmacological effect of a non-steroidal acid anti-inflammatory agent selected from the group consisting of phenylbutazone, ibuprofen, mefenamic acid, indomethacin, acetylsalicylic acid, naproxen, ketoprofen and flurbiprofen, when administered to a subject which comprises orally administering a therapeutically effective amount of a combination of said non-steroidal acidic anti-inflammatory agent with a potentiating effective amount of 4-ethoxy-2-methyl-5-morpholino-3(2H)-pyridazinone, said combination comprising about ¼ to ½ of the oral clinically effective amount of 4-ethoxy-2-methyl-5-morpholino-3(2H)-pyridazinone and about ⅓ to ½ the oral clinically effective amount of the non-steroidal acidic anti-inflammatory agent.

4. A process for treating a subject suffering from pain and/or inflammation which comprises orally administering to said subject a therapeutically effective amount of the composition of claim 1.

* * * * *